United States Patent [19]
Adair et al.

[11] Patent Number: 5,994,510
[45] Date of Patent: Nov. 30, 1999

[54] RECOMBINANT ANTIBODIES SPECIFIC FOR TNFα

[75] Inventors: John Robert Adair, Bucks; Diljeet Singh Athwal, London; John Spencer Emtage, Bucks; Mark William Bodmer, Oxford, all of United Kingdom

[73] Assignee: Celltech Therapeutics Limited, Slough, United Kingdom

[21] Appl. No.: 08/456,418

[22] Filed: Jun. 1, 1995

Related U.S. Application Data

[62] Continuation of application No. 08/373,882, Jan. 17, 1995, abandoned, which is a continuation of application No. 07/920,378, filed as application No. PCT/GB91/02300, Dec. 20, 1991, abandoned.

[30] Foreign Application Priority Data

Dec. 21, 1990 [WO] WIPO ...................... PCT/GB90/02017
May 3, 1991 [GB] United Kingdom ................... 9109645

[51] Int. Cl.⁶ .................................................. C07K 16/24
[52] U.S. Cl. ..................... 530/387.3; 530/387.1; 530/388.22; 530/389.2
[58] Field of Search ....................... 424/145.1; 435/69.6, 435/172.3, 240.27, 320; 935/15; 530/388.22

[56] References Cited

FOREIGN PATENT DOCUMENTS

| | | |
|---|---|---|
| 0 355 067 | 2/1990 | European Pat. Off. . |
| 0 365 209 A2 | 4/1990 | European Pat. Off. . |
| 0 403 156 | 12/1990 | European Pat. Off. . |
| WO 90/07861 | 7/1990 | WIPO . |
| WO 91/09967 | 7/1991 | WIPO . |
| WO 92/04381 | 3/1992 | WIPO . |
| WO 92/15683 | 9/1992 | WIPO . |
| WO 92/16553 | 10/1992 | WIPO . |

OTHER PUBLICATIONS

Opal, Steven M., et al., "Efficacy of a Monoclonal Antibody Directed Against Tumor Necrosis Factor in Protecting Neutropenic Rats from Lethal Infection with Pseudomonas aeruginosa," Journal of Infectious Diseases, vol. 161, No. 6, Jun. 1990, pp. 1148–1152.

Queen, Cary, et al., "A Humanized Antibody That Binds to the Interleukin 2 Receptor," Proceedings of the National Academy of Sciences, USA, vol. 86, No. 24, Dec. 1989, pp. 10029–10033.

Roberts et al, "Generation of Antibody with Enhanced Affinity and Specificity for its Antigen by Protein Engineering" Nature, 328(20):731–734, Aug., 1987.

Verhoeyen et al, "Reshaping Human Antibodies: Grafting an Antilysozyme Activity", Science, 239:1534–36 Mar. 25, 1988.

Levitt, J. of Molec Biol. 168: 595–657 (1983) "Molecular Dynamics of Native Protein".

Whittle et al, J. of Cellular Biochemistry, Suppl. 13A, p. 96 1989, "Construction and Expression of a CDR–grafted anti—TNF antibody".

Stevens et al, Transplantation, 50: 856–861 (Nov. 1990).

Leevwenberg et al, Eur. J. Imm., 18: 1469–1472 (1988).

*Primary Examiner*—Nancy A Johnson
*Attorney, Agent, or Firm*—Woodcock Washburn Kurtz Mackiewicz & Norris LLP

[57] ABSTRACT

Recombinant, in particular humanised, e.g. humanised chimeric and CDR-grafted humanised, antibody molecules having specificity for human TNFα, are provided for use in diagnosis and therapy. In particular, the antibody molecules have antigen binding sites derived from murine monoclonal antibodies CB0006, CB0010, hTNF3 or 101.4. Preferred CDR-grafted humanised anti-hTNFα antibodies comprise variable region domains comprising human acceptor framework and donor antigen binding regions and wherein the frameworks comprise donor residues at specific positions. The antibody molecules may be used for therapeutic treatment of human patients suffering from or at risk of disorders associated with undesirably high levels of TNF, in particular for treatment of immunoregulatory and inflammatory disorders or of septic, endotoxic or cardiovascular shock.

3 Claims, 6 Drawing Sheets

CDR GRAFTING OF hTNF-1

Light Chain Data

```
1 Eu    DIQMTQSPST LSASVGDRVT ITCRASQSI. ....NTWLA  WYQQKPGKAPK
htnf1   DIMMSQSPSS LAVSVGEKVTMS CKSSQSLLYSNNQKNYLA WYQQKPGQSPK
g Eu    DIMMTQSPST LSASVGDRVTIT CKSSQSLLYSNNQKNYLA WYQQKPGQAPK Eu      LLMYKASSLE SGVPSRFIGS GSGTEFTLTI SSLQPDDFAT YYCQQYNSDS
htnf1   LLISWASTRES GVPDRFTGS GSGTDFTLTI SSVKAEDLAV YYCQQYYDYP
gEu     LLISWASTRES GVPSRFIGS GSGTEFTLTI SSLQPDDVAT YYCQQYYDYP 3 Eu    KMFGQG TKVEVKG..(KAPPA)
htnf1   WTFGGG SKLEIK.....anti human TNF seq from
g Eu    WTFGQG TKVEIKR..(KAPPA)
``` framework residues changed (# = Kabat)

chgs 3/42/48/49/83/106/108

Heavy Chain Data

```
Eu      QVQLVQSGAE VKKPGSSVKV SCKASGGTFSRSAII WVRQA PGQGLEWMGG
htnf1   EVLLQQSGPE LVKPGASVKI PCKASGYTFTDYNVD WVKQS HGKSLQWIGN
2hEug   QVQLVQSGAE VVKPGSSVKV SCKASGYTFTDYNVD WVKQA PGQGLQWIGN Eu      IVPMFGPPNYAQKFQG  RVTITADESTNTAYMELSSLRSED  TAFYFCAGGY
htnf1   INPNNGGTIYNQKFKG  KGTLTVDKSSSTAYMELRSLTSED  TAVYYCARSA
2hEug   INPNNGGTIYNQKFKG  KGTLTVDKSTSTAYMELSSLTSED  TAVYYCARSA Eu      GIYSPE           WGQGTLVTVSS.grp 1kabat cdr chg frwk4
htnf1   FYNNYEYFDV       WGAGTTVTVSS
2hEug   FYNNYEYFDV       WGQGTTVTVSS
``` framework residues changed (# = kabat)

chgs 12/27/30/38/46/48/66/67/69/71/73/76/83/89/91/94/108

Fig. 1

CDR GRAFTING OF 101-4

LIGHT CHAIN SUMMARY

```
1 rei     DIQMTQSPSS LSASVGDRVT ITCQASQDI. ....IKYLNW YQQTPGKAPK
101/4     QIVLTQSPPI MSASPGEKVT MTCSASSSVSFMY        W YQQKPGSSPR
g1014     QIVLTQSPSS LSASVGDRVT ITCSASSSVSFMY        W YQQKPGKAPK 2 rei     LLIYEASNLQA GVPSRFSGS GSGTDYTFTI SSLQPEDIAT YYCQQYQSLP
101/4     LLIYDASILAS GVPVRFSGS GSGTSYSLTI SRMEAEDVAT YYCQQWSDYS
g1014     LLIYDASILAS GVPSRFSGS GSGTDYTLTI SSLQPEDIAT YYCQQWSDYS 3 rei      YTFGQGTKLQ ITR..celltech rei
101/4      PRTFGGGTKLE IKR.....THIS IS MOUSE(INSERTION IN CDR3)JSE
g1014      PRTFGQGTKVE IKR..celltech rei
``` framework residues changed (# = Kabat)

1/3/4/39/73/104/105/107

HEAVY CHAIN SUMMARY

```
                23                                         48
KOL     QVQLVESGGG VVQPGRSLRL SCSSSGFIFSSYAMY WVRQA PGKGLEWVAI
101/4   EVKIEESGGG WVQPGGSMKL SCIASGFTFSNYWMN WVRQS PEKGLEWVAE
g1014   QVQIVESGGG WVQPGRSLRL SCIASGFTFSNYWMN WVRQA PGKGLEWVAE 71                          88
KOL     IWDDGSDQHYADSVKG  RFTISRDNSKNTLFLQMDSLRPED TGVYFCARDG
101/4   VRLQSDNFTTHYAESVKGRFTISRDDSKSGVYLQMNNLGAED TGIYYCTPFA
g1014   VRLQSDNFTTHYAESVKGRFTISRDDSKNGVYLQMDSLRPED TGVYYCTPFA

KOL     GHGFCSSASCFGPDY WGQGTPVTVSS....HUMAN(kabat CDR defn)
101/4                 Y WGQGTLVTVSP...MOUSE seq
g1014                 Y WGQGTLVTVSS
``` framework residues changed (# = Kabat)

LIGHT CHAIN SUMMARY

REI     DIQMTQSPSS LSASVGDRVT ITCQASQDI. ....IKYLN WYQQTPGKAPK
CB6     SIVMTQTPKF LLVSAGDRVT ITCKASQSVS NDVA      WYQQKSGQSPK
gCB6    DIQMTQSPSS LSASVGDRVT ITCKASQSVS NDVA      WYQQTPGKAPK

REI     LLIYEASNLQA GVPSRFSGS GSGTDYTFTI SSLQPEDIAT YYCQQYQSLP
CB6     VLIYHVSNRYT GVPDRFTGS GYGTDFTFTI TTVQAEDLAV YFCQQDYSSP
gCB6    LLIYHVSNRYT GVPSRFSGS GSGTDYTFTI SSLQPEDIAT YYCQQDYSSP

REI     YTFGQGTKLQ ITR... celltech rei(KAPPA)
CB6      WTFGGGTKLE IK.... MOUSE AB... REI (NO FWRKS)
gCB6    WTFGQGTKLQ ITR... grafted AB sequence

HEAVY CHAIN SUMMARY

KOL     QVQLVESGGG VVQPGRSLRL SCSSSGFIFSSYAMY WVRQA PGKGLEWVAI
CB6     QIQLVQSGPD LKKPGETVKI SCKASGYTFTNYGMN WVKQT PGKGLKWMGW
gCB6    QVQLVESGGG VVQPGRSLRL SCKASGYTFTNYGMN WVRQA PGKGLEWMGW

KOL     IWDDGSDQHYADSVKG RFTISRDNSKNTLFLQMDSLRPED TGVYFCARDG
CB6     INTYTGEPTYDDDFKG RPAFSLEASASTAYLQINNLKNED MATFFCARQE
gCB6    INTYTGEPTYDDDFKG RFTISLDASKNTLFLQMDSLRPED TGVYFCARQE

KOL     GHGFCSSASCFGPDY WGQGTPVTVS.HUMAN grp3(kabat CDR defn)
CB6             GFYAMDY WGQGTSLTVSS..MOUSE ANTI-TNF sequence
gCB6            GFYAMDY WGQGTPVTVS.grafted AB sequence
```

Fig. 3 hTNF3

LIGHT CHAIN SUMMARY

```
REI     DIQMTQSPSS LSASVGDRVT ITCQASQDI. ....IKYLN WYQQTPGKAPK
HTNF3   NIVMTQTPKF LLVSAGDRIT ITCKASQSVS NDVA      WYQQKPGQSPR
gHTNF3  DIQMTQSPSS LSASVGDRVT ITCKASQSVS NDVA      WYQQTPGKAPK

REI     LLIYEASNLQA GVPSRFSGS GSGTDYTFTI SSLQPEDIAT YYCQQYQSLP
HTNF3   LLIYYVSNRYT GVPDRFTGS GYGTDFTFTI NTVQAEDLAY YFCQQDYSSP
gHTNF3  LLIYYVSNRYT GVPSRFSGS GSGTDYTFTI SSLQPEDIAT YYCQQDYSSP

REI     YTFGQGTKLQ ITR.. (KAPPA)
HTNF3   YTFGGGTRLE VK.... MOUSE AB sequence
gHTNF3  YTFGQGTKLQ ITR..grafted sequence
```

HEAVY CHAIN SUMMARY

```
KOL     QVQLVESGGG VVQPGRSLRL SCSSSGFIFSSYAMY WVRQA PGKGLEWVAI
hTNF3   RIQLVQSGPE LKKPGETVKI SCKASGYTFTNYGMN  WVTQA PGKGLKWMGW
ghTNF3  QVQLVESGGG VVQPGRSLRL SCKASGYTFTNYGMN  WVRQA PGKGLEWMGW

KOL     IWDDGSDQHYADSVKG RFTISRDNSKNTLFLQMDSLRPED TGVYFCARDG
hTNF3   INTYTGEPTYADDFKG RFAFSLETSASTAYLQINNLKNED TATYFCARKE
ghTNF3  INTYTGEPTYADDFKG RFTISLDTSKNTLFLQMDSLRPED TGVYFCARKE

KOL     GHGFCSSASCFGPDY WGQGTPVTVS.HUMAN grp3
hTNF3           GFYAMDY WGQGTSVTVSS...MOUSE.ANTI-TNF sequence
ghTNF3          GFYAMDY WGQGTPVTVS.grafted AB sequence
```

Fig. 4

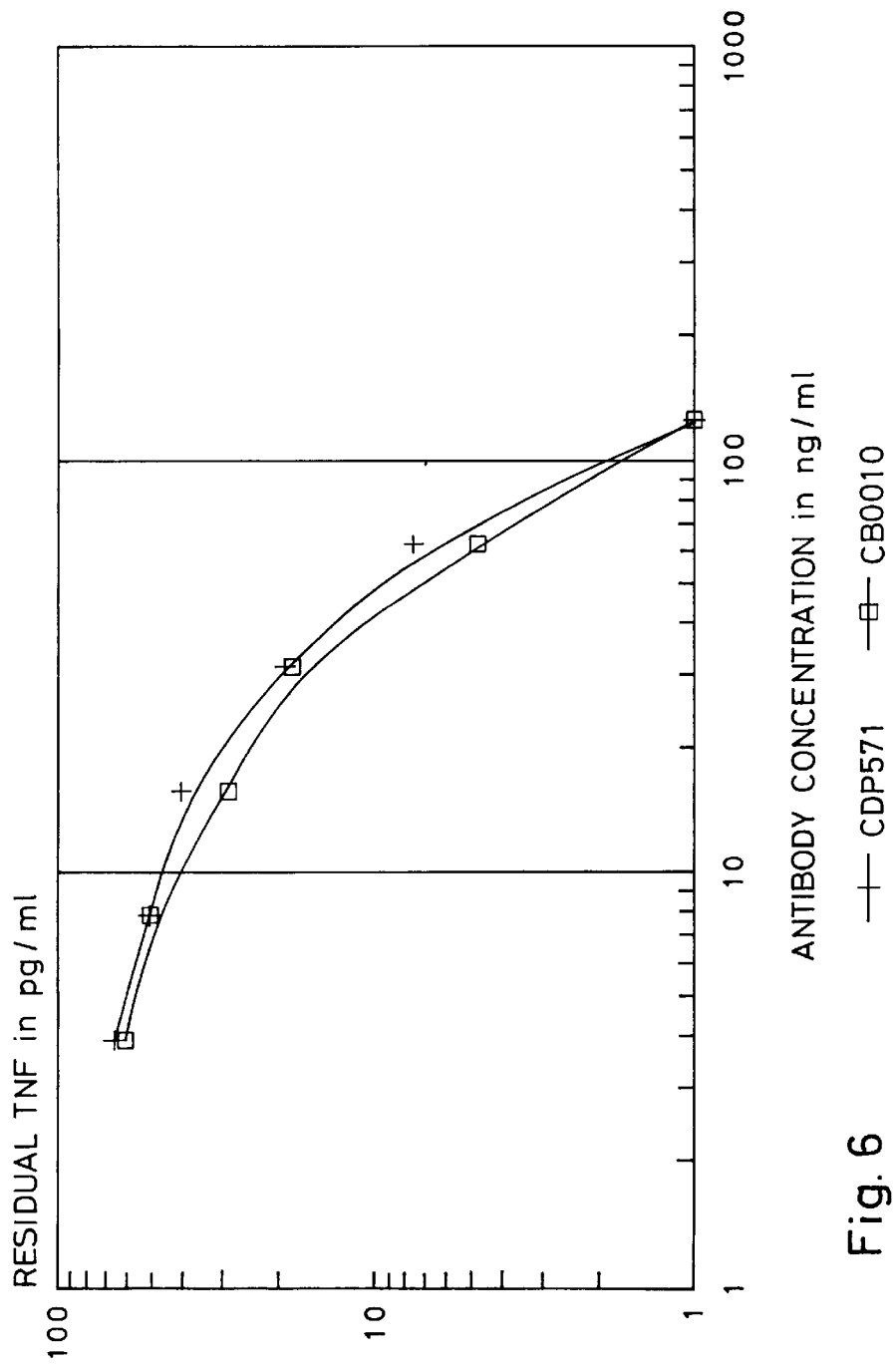

“RECOMBINANT ANTIBODIES SPECIFIC FOR TNFα”

This is a continuation, of application Ser. No. 08/373,882; Filed Jan. 17, 1995, which is §1.62 Continuation of Ser. No. 07/920,378, filed Sep. 28, 1992, now abandoned, which is a national phase filing of PCT/GB91/02300, filed Dec. 20, 1991 claiming priority of PCT application PCT/GB90/02017 filed Dec. 21, 1990 and United Kingdom Application 9109645.3, filed May 03, 1991.

FIELD OF THE INVENTION

This invention relates to recombinant, in particular humanised, antibody molecules having specificity for antigenic determinants of tumour necrosis factor alpha (TNF-α), to processes for their production using recombinant DNA technology, and to their therapeutic uses.

For the purposes of the present description the term "recombinant antibody molecule" is used to describe an antibody molecule produced by any process involving the use of recombinant DNA technology, including any analogues of natural immunoglobulins or their fragments.

Also for the purposes of the present description the term "humanised antibody molecule" is used to describe a molecule having an antigen binding site derived from an immunoglobulin from a non-human species, and remaining immunoglobulin derived parts of the molecule being derived from a human immunoglobulin. Thus humanised antibody molecules include humanised chimeric antibody molecules comprising complete non-human heavy and/or light chain variable region domains linked to human constant region domains. Humanised antibody molecules also comprise CDR-grafted humanised antibody molecules comprising one or more CDRs from a non-human antibody grafted into a heavy and/or light chain human variable region framework.

The antigen binding specificity of antibodies is determined by their complementarily determining regions (CDRs) which are relatively short peptide sequences carried on the framework regions of the variable domains. There are 3CDRs, (CDR1, CDR2 and CDR3) in each of the heavy and light chain variable domains.

The abbreviation "MAb" is used to indicate a monoclonal antibody. In the present description reference is made to a number of publications by number, and these publications are listed in numerical order at the end of the description.

BACKGROUND OF THE INVENTION

Natural immunoglobulins have been known for many years, as have the various fragments thereof, such as the Fab, Fv, (Fab')$_2$ and Fc fragments, which can be derived by enzymatic cleavage. Natural immunoglobulins comprise a generally Y-shaped molecule having an antigen-binding site towards the end of each upper arm. The remainder of the structure, and particularly the stem of the Y, mediates the effector functions associated with immunoglobulins.

Natural immunoglobulins have been used in assay, diagnosis and, to a more limited extent, therapy. However, such uses, especially in therapy, were hindered until recently by the polyclonal nature of natural immunoglobulins. A significant step towards the realisation of the potential of immunoglobulins as therapeutic agents was the discovery of procedures for the reproducible production of monoclonal antibodies (MAbs) of defined specificity (1).

However, most MAbs are produced by hybridomas which are fusions of rodent spleen cells with rodent myeloma cells. They are therefore essentially rodent proteins. There are very few reports of the production of human MAbs.

Since most available MAbs are of rodent origin, they are naturally antigenic in humans and thus can give rise to an undesirable immune response termed the HAMA (Human Anti-Mouse Antibody) response if the MAb is administered to a human. Therefore, the use of rodent MAbs as therapeutic agents in humans is inherently limited by the fact that the human subject will mount an immunological response to the MAb and will either remove it entirely or at least reduce its effectiveness. In practice, MAbs of rodent origin may not be used in patients for more than one or a few treatments as a HAMA response soon develops rendering the MAb ineffective as well as giving rise to undesirable reactions. For instance, OKT3 a mouse IgG2a/k MAb which recognises an antigen in the T-cell receptor-CD3 complex has been approved for use in many countries throughout the world as an immunosuppressant in the treatment of acute allograft rejection [Chatenoud et al (2) and Jeffers et al (3)]. However, in view of the rodent nature of this and other such MAbs, a significant HAMA response which may include a major anti-idiotype component, may build up on use. Clearly, it would be highly desirable to diminish or abolish this undesirable HAMA response and thus enlarge the areas of use of such antibodies.

Proposals have therefore been made to render non-human MAbs less antigenic in humans. Such techniques can be generically termed "humanisation" techniques. These techniques typically involve the use of recombinant DNA technology to manipulate DNA sequences encoding the polypeptide chains of the antibody molecule.

Early methods for humanising MAbs involved production of chimeric antibodies in which an antigen binding site comprising the complete variable domains of one antibody is linked to constant domains derived from another antibody. Methods for carrying out such chimerisation procedures are described in EP0120694 (Celltech Limited), EP0125023 (Genentech Inc. and City of Hope), EP-A-0 171496 (Res. Dev. Corp. Japan), EP-A-0 173 494 (Stanford University), and WO 86/01533 (Celltech Limited). These prior patent applications generally disclose processes for preparing antibody molecules having the variable domains from a mouse MAb and the constant domains from a human immunoglobulin. Such humanised chimeric antibodies, however, still contain a significant proportion of non-human amino acid sequence, i.e. the complete non-human variable domains, and thus may still elicit some HAMA response, particularly if administered over a prolonged period [Begent et al (ref. 4)].

In an alternative approach, described in EP-A-0239400 (Winter), the complementarity determining regions (CDRs) of a mouse MAb have been grafted onto the framework regions of the variable domains of a human immunoglobulin by site directed mutagenesis using long oligonucleotides. Such CDR-grafted humanised antibodies are much less likely to give rise to a HAMA response than humanised chimeric antibodies in view of the much lower proportion of non-human amino acid sequence which they contain.

The earliest work on humanising MAbs by CDR-grafting was carried out on MAbs recognising synthetic antigens, such as the NP or NIP antigens. However, examples in which a mouse MAb recognising lysozyme and a rat MAb recognising an antigen on human T-cells were humanised by CDR-grafting have been described by Verhoeyen et al (5) and Riechmann et al (6) respectively. The preparation of CDR-grafted antibody to the antigen on human T cells is also described in WO 89/07452 (Medical Research Council).

In Riechmann et al/Medical Research Council it was found that transfer of the CDR regions alone [as defined by Kabat refs. (7) and (8)] was not sufficient to provide satisfactory antigen binding activity in the CDR-grafted product. Riechmann et al found that it was necessary to convert a serine residue at position 27 of the human heavy chain sequence to the corresponding rat phenylalanine residue to obtain a CDR-grafted product having improved antigen binding activity. This residue at position 27 of the heavy chain is within the structural loop adjacent to CDR1. A further construct which additionally contained a human serine to rat tyrosine change at position 30 of the heavy chain did not have a significantly altered binding activity over the humanised antibody with the serine to phenylalanine change at position 27 alone. These results indicated that changes to residues of the human sequence outside the CDR regions, in particular in the structural loop adjacent to CDR1 of the heavy chain, may be necessary to obtain effective antigen binding activity for CDR-grafted antibodies which recognise more complex antigens. Even so the binding affinity of the best CDR-grafted antibodies obtained was still significantly less than the original MAb.

Recently Queen et al (9) have described the preparation of a humanised antibody that binds to an interleukin 2 receptor, by combining the CDRs of a murine MAb (anti-Tac) with human immunoglobulin framework and constant regions. The human framework regions were chosen to maximise homology with the anti-Tac MAb sequence. In addition computer modelling was used to identify framework amino acid residues which were likely to interact with the CDRs or antigen, and mouse amino acids were used at these positions in the humanised antibody.

In WO90/07861 Queen et al propose four criteria for designing humanised immunoglobulins. The first criterion is to use as the human acceptor the framework from a particular human immunoglobulin that is unusually homologous to the non-human donor immunoglobulin to be humanised, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs. The fourth criterion is to use the donor amino acid residue at framework positions at which the amino acid is predicted to have a side chain atom within about 3 Å of the CDRs in a three-dimensional immunoglobulin model and to be capable of interacting with the antigen or with the CDRs of the humanised immunoglobulin. It is proposed that the second, third or fourth criteria may be applied in addition or alternatively to the first criterion, and may be applied singly or in any combination.

WO90/07861 describes in detail the preparation of a single CDR-grafted humanised antibody, a humanised antibody having specificity for the p55 Tac protein of the IL-2 receptor. The combination of all four criteria, as above, were employed in designing this humanised antibody, the variable region frameworks of the human antibody EU (7) being used as acceptor. In the resultant humanised antibody the donor CDRs were as defined by Kabat et al (7 and 8) and in addition the mouse donor residues were used in place of the human acceptor residues, at positions 27, 30, 48, 66, 67, 89, 91, 94, 103, 104, 105 and 107 in the heavy chain and at positions 48, 60 and 63 in the light chain, of the variable region frameworks. The humanised anti-Tac antibody obtained is reported to have an affinity for p55 of $3 \times 10^9$ M$^{-1}$, about one-third of that of the murine MAb.

We have further investigated the preparation of CDR-grafted humanised antibody molecules and have identified a hierarchy of positions within the framework of the variable regions (i.e. outside both the Kabat CDRs and structural loops of the variable regions) at which the amino acid identities of the residues are important for obtaining CDR-grafted products with satisfactory binding affinity. This has enabled us to establish a protocol for obtaining satisfactory CDR-grafted products which may be applied very widely irrespective of the level of homology between the donor immunoglobulin and acceptor framework. The set of residues which we have identified as being of critical importance overlaps but does not coincide with the residues identified by Queen et al (9). Our copending International patent application WO91/09967 describes this protocol for the preparation of CDR-grafted, in particular humanised, antibody heavy and light chains and complete molecules of any desired specificity. The full disclosure of International patent application WO/91/09967 is incorporated in the present description by reference.

Tempest et al (10) have very recently described the preparation of a reshaped human monoclonal antibody for use in inhibiting human respiratory syncytial virus (RSV) infection in vivo. This reshaped antibody was prepared by grafting synthetic oligo nucleotides coding for the CDRs of a murine MAb, which neutralises RSV infection, by site-directed mutagenesis into DNA coding for the frameworks of a human IgG1, monoclonal antibody. However the simple reshaped antibody in which the CDRs alone had been transferred between mouse and human antibodies had only very poor binding for RSV which was not significantly above background. In order to partially restore binding ability it proved necessary to additionally convert human residues to mouse residues in a framework region adjacent to CDR3 of the heavy chain. Tempest et al did not convert human residues to mouse residues at important positions identified in the protocol of WO91/09967. TNFα is a cytokine which is released by and interacts with cells of the immune system. Thus TNFα is released by macrophages which have been activated by lipopoly-saccharide (LPS) of gram negative bacteria. As such TNFα appears to be an endogenous mediator of central importance involved in the development and pathogenesis of endotoxic shock associated with bacterial sepsis. Antibodies to TNFα has been proposed for the prophylaxis and treatment of endotoxic shock (Beutler et al (11)). However the antibodies to TNFα currently available for use in such treatment are typically murine MAbs. As such these murine MAbs are of only limited use for treatment of humans in view of the undesirable HAMA (Human Anti-Mouse Antibody) response which they can elicit if used for more than one or a few treatments. It is thus a highly desirable objective to prepare humanised anti-TNFα products for use in human therapy.

Our co-pending International patent application WO91/09967 describes, among other things, the preparation of humanised CDR-grafted antibody products which have specificity for TNFα. In particular WO91/09967 describes, in Example 5, preparation of specific humanised CDR grafted antibodies to human TNFα derived from the murine anti-human TNFα MAbs identified as 61E71 (alternatively known as CB0006), hTNF1 (alternatively known as CB0010), hTNF3 and 101.4. The present application relates specifically to recombinant, in particular humanised antibodies to human TNFα, including those described in WO91/09967 and further improved humanised CDR-grafted antibodies to human TNFα based upon the hTNF1 (CB0010) and 101.4 murine MAbs. Further studies of various anti-human TNFα murine MAbs have revealed that hTNF1 and 101.4 have particularly desirable properties for use in anti-TNF therapy.

SUMMARY OF THE INVENTION

Accordingly the present invention provides recombinant antibody molecules which have specificity for human TNFα.

The recombinant antibody molecules of the invention are preferably TNF neutralising, i.e. are capable of reducing or inhibiting a biological activity of human TNFα as measured by an in vitro or in vivo test.

Preferably the invention provides recombinant antibody molecules having antigen binding sites derived from the murine MAbs CB0006. CB0010, hTNF3 or 101.4, especially from the murine MAbs CB0010 or 101.4.

Preferably the recombinant antibody molecules of the invention are humanised antibody molecules including both chimeric humanised antibody molecules and CDR-grafted humanised antibody molecules.

For the purposes of the present description a "chimeric humanised antibody molecule" comprises complete non-human (e.g. murine MAb) variable domains linked to human constant domains, and a "CDR-grafted humanised antibody molecule" comprises an antibody heavy and/or light chain containing one or more CDRs from a non-human antibody (e.g. a murine MAb) grafted into a human heavy and/or light chain variable region framework.

The CDR-grafted humanised anti-TNFα antibody products of this invention include anti-human TNFα antibody heavy and light chain and molecule products as defined in the first, second, third and fourth aspects of the invention described in WO91/09967.

DETAILED DESCRIPTION OF THE INVENTION

Thus in first preferred embodiments, the invention provides a CDR-grafted humanised anti-hTNFα antibody heavy chain having a variable region domain comprising human acceptor framework and donor antigen binding regions wherein the framework comprises donor residues at at least one of positions 6, 23 and/or 24, 48 and/or 49, 71 and/or 73, 75 and/or 76 and/or 78 and 88 and/or 91.

Preferably in these first preferred embodiments, the heavy chain framework comprises donor residues at positions 23, 24, 49, 71, 73 and 78 or at positions 23, 24 and 49. The residues at positions 71, 73 and 78 of the heavy chain framework are preferably either all acceptor or all donor residues.

Especially in these first preferred embodiments the heavy chain framework additionally comprises donor residues at one, some or all of positions 6, 37, 48 and 94. Also it is particularly preferred that residues at positions of the heavy chain framework which are commonly conserved across species, i.e. positions 2, 4, 25, 36, 39, 47, 93, 103, 104, 106 and 107, if not conserved between donor and acceptor, additionally comprise donor residues. Most preferably the heavy chain framework additionally comprises donor residues at positions 2, 4, 6, 25, 36, 37, 39, 47, 48, 93, 94, 103, 104, 106 and 107.

In addition the heavy chain framework optionally comprises donor residues at one, some or all of positions:
1 and 3,
72 and 76,
69 (if 48 is different between donor and acceptor),
38 and 46 (if 48 is the donor residue),
80 and 20 (if 69 is the donor residue),
67,
82 and 18 (if 67 is the donor residue),
91,
88, and
any one or more of 9, 11, 41, 87, 108, 110 and 112.

In the present description, typically the donor antibody is a non-human anti-hTNFα antibody, such as a rodent MAb, and the acceptor antibody is a human antibody.

In the CDR-grafted humanised anti-hTNFα antibodies of the present invention, the donor antigen binding region typically comprises at least one CDR from the donor antibody. Usually the donor antigen binding region comprises at least two and preferably all three CDRs of each of the heavy chain and/or light chain variable regions. The CDRs may comprise the Kabat CDRs, the structural loop CDRs or a composite of the Kabat and structural loop CDRs and any combination of any of these.

Preferably, the antigen binding regions of the CDR-grafted heavy chain variable domain comprise CDRs corresponding to the Kabat CDRs at CDR2 (residues 50–65) and CDR3 (residues 95–102) and a composite of the Kabat and structural loop CDRs at CDR1 (residues 26–35). These preferred CDR designations are preferably used for the CDR-grafted heavy chains of the first preferred embodiments, i.e. residues 26–30 are included within CDR1.

The residue designations given above and elsewhere in the present application are numbered according to the Kabat numbering [refs. (7) and (8)]. Thus the residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. For example, the heavy chain variable region of the anti-Tac antibody described by Queen et al (9) contains a single amino acid insert (residue 52a) after residue 52 of CDR2 and a three amino acid insert (residues 82a, 82b and 82c) after framework residue 82, in the Kabat numbering. The correct Kabat numbering of residues may be determined for a given antibody by alignment at regions of homology of the sequence of the antibody with a "standard" Kabat numbered sequence.

It will be appreciated that when the CDR-grafted humanised antibody molecule embodiments of the invention, as described above and elsewhere in the present description, are applied to a particular donor/acceptor antibody pair, in some cases the donor and acceptor amino acid residues may be identical at a particular position identified for change to the donor residue, and thus no change or acceptor framework residue is required.

The invention also provides in second preferred embodiments a CDR-grafted humanised anti-hTNFα antibody light chain having a variable region domain comprising human acceptor framework and donor antigen binding regions wherein the framework comprises donor residues at at least one of positions 1 and/or 3 and 46 and/or 47.

Preferably the CDR grafted light chain of the second preferred embodiment comprises donor residues at positions 46 and/or 47.

The invention also provides in third preferred embodiments a CDR-grafted humanised anti-hTNFα antibody light chain having a variable region domain comprising human acceptor framework and donor antigen binding regions wherein the framework comprises donor residues at at least one of positions 46, 48, 58 and 71.

In the third preferred embodiments, the framework preferably comprises donor residues at all of positions 46, 48, 58 and 71.

In particularly preferred embodiments of the second and third preferred embodiments, the framework additionally comprises donor residues at positions 36, 44, 47, 85 and 87. Similarly positions of the light chain framework which are commonly conserved across species, i.e. positions 2, 4, 6, 35, 49, 62, 64–69, 98, 99, 101 and 102, if not conserved between donor and human acceptor, additionally comprise donor residues. Most preferably the light chain framework additionally comprises donor residues at positions 2, 4, 6, 35, 36, 38, 44, 47, 49, 62, 64–69, 85, 87, 98, 99, 101 and 102.

In addition the framework of the second or third preferred embodiments optionally comprises donor residues at one, some or all of positions:
1 and 3,
63,
60 (if 60 and 54 are able to form at potential saltbridge),
70 (if 70 and 24 are able to form a potential saltbridge),
73 and 21 (if 47 is different between donor and acceptor),
37 and 45 (if 47 is different between donor and acceptor),
and
any one or more of 10, 12, 40, 80, 103 and 105.

Preferably, the antigen binding regions of the CDR-grafted light chain variable domain, including those of the second and third preferred embodiments described above, comprise CDRs corresponding to the Kabat CDRs at CDR1 (residue 24–34), CDR2 (residues 50–56) and CDR3 (residues 89–97).

The invention further provides in a fourth preferred embodiment a CDR-grafted antibody molecule comprising at least one CDR-grafted heavy chain and at least one CDR-grafted light chain according to the first and second or first and third preferred embodiments of the invention.

In a first particularly preferred embodiment, however, the invention provides a CDR-grafted humanised antibody heavy chain having a variable region domain comprising human acceptor framework (especially EU human acceptor framework) and hTNF1 donor antigen binding regions wherein the framework comprises hTNF1 donor residues at positions 12, 27, 30, 38, 46, 48, 66, 67, 69, 71, 73, 76, 83, 89, 91 and 94.

The EU heavy chain framework has residues in framework 4 (FR4) of the heavy chain which are anomalous for human heavy chain frameworks. Thus preferably human consensus residues are used in place of EU residues in FR4 of the heavy chain. In particular, the human consensus residue threonine (T) may be used at position 108. Fortuitously the murine hTNF1 residue at position 108 is also threonine.

In a second particularly preferred embodiment the invention provides a CDR-grafted humanised antibody light chain having a variable domain comprising human acceptor framework (especially EU human acceptor framework) and hTNF1 donor antigen binding regions wherein the framework comprises hTNF1 donor residues at positions 3, 42 and 49.

When the EU human framework is used for the light chain it is also desirable to change residues from EU residues at positions 48, 83, 106 and 108, as the EU residues at these positions are anomalous for human antibodies. Thus the human consensus residues may be used at some or preferably all of these residues, i.e. isoleucine (I) at position 48, valine (V) at position 83, isoleucine (I) at position 106 and arginine (R) at position 108. Fortuitously the murine hTNF1 residues are the same as the human consensus residues at positions 48 (I), 106 (I) and 108 (R). However, the human consensus residue valine (V) at position 83 differs from both the EU residue (F) and the hTNF1 residue (L) at this position.

Especially the invention includes CDR-grafted humanised antibody molecules comprising at least one CDR-grafted humanised heavy chain according to the first particularly preferred embodiment and at least one CDR-grafted humanised light chain according to the second particularly preferred embodiment.

Also in a third particularly preferred embodiment the invention provides a CDR-grafted humanised antibody heavy chain having a variable region domain comprising human acceptor framework (especially KOL human acceptor framework) and 101.4 donor antigen binding regions wherein the framework comprises 101.4 donor residues at positions 4, 11, 23, 24, 28, 73, 77, 78, 79, 91, 93 and 94.

The KOL residue proline (P) at position 108 of the heavy chain is anomalous for human antibodies. Thus preferably the human consensus residue leucine (L) is at this position if KOL is used as the human acceptor framework. Fortuitously the murine 101.4 antibody has the human consensus residue (L) at this position.

Moreover in a fourth particularly preferred embodiment the invention provides a CDR-grafted humanised antibody light chain having a variable region domain comprising human acceptor framework (especially REI human acceptor framework) and 101.4 donor residues at positions 1, 3, 4 and 73.

The REI light chain human framework has residues which are anomalous for human antibodies at positions 39 (threonine, T), 104 (leucine, L), 105 (glutamine, Q), and 107 (threonine, T). Thus when REI is used as the light chain framework, human consensus residues are used at positions 39 (lysine, K), 104 (valine, V), 105 (glutamic acid, E) and 107 (lysine, K). Fortuitously the murine 101.4 residues are the same as the human consensus residues at positions 39 (K), 105 (E) and 107 (K). However, the human consensus residue at position 104 (V) differs from the leucine (L) REI and murine 101.4 residues at this position.

Especially also the invention includes CDR grafted humanised antibody molecules comprising at least one CDR-grafted humanised heavy chain according to the third particularly preferred embodiment and at least one CDR-grafted humanised light chain according to the fourth particularly preferred embodiment.

Preferably the Kabat CDRs are used for all of the CDRs (CDR1, CDR2 and CDR3) of both the heavy and light chains of the first, second, third and fourth particularly preferred embodiments described above.

The recombinant and humanised antibody molecules and chains of the present invention may comprise: a complete antibody molecule, having full length heavy and light chains; a fragment thereof, such as a Fab, Fab', F(ab')$_2$ or Fv fragment; a light chain or heavy chain monomer or dimer; or a single chain antibody, e.g. a single chain Fv in which heavy and light chain variable regions are joined by a peptide linker; or any other recombinant, chimeric or CDR-grafted molecule with the same specificity as the original donor antibodies. Similarly the heavy and light chain variable region may be combined with other antibody domains as appropriate.

Also the heavy or light chains or recombinant or humanised complete antibody molecules of the present invention may have attached to them an effector or reporter molecule.

For instance, it may have a macrocycle, for chelating a heavy metal atom, or a toxin, such as ricin, attached to it by a covalent bridging structure. Alternatively, the procedures of recombinant DNA technology may be used to produce an immunoglobulin molecule in which the Fc fragment or CH3 domain of a complete immunoglobulin molecule has been replaced by, or has attached thereto by peptide linkage, a functional non-immunoglobulin protein, such as an enzyme or toxin molecule.

The amino acid sequences of the heavy and light chain variable domains of the CB0010, 101.4, CB0006 and hTNF3 murine MAbs, CDR-grafted variants thereof and human acceptor antibodies are given in the accompanying diagrams FIGS. 1, 2, 3 and 4 respectively. The recombinant and humanised antibody products of the invention may be prepared using recombinant DNA techniques, for instance substantially as described in WO91/09967.

Any appropriate human acceptor variable region framework sequences may be used having regard to class/type of the donor antibody from which the antigen binding regions are derived. Preferably, the type of human acceptor framework used is of the same/similar class/type as the donor antibody. Conveniently, the framework may be chosen to maximise/optimise homology with the donor antibody sequence particularly at positions close or adjacent to the CDRs. However, a high level of homology between donor and acceptor sequences is not critical for application of the present invention. The present invention identifies a hierarchy of framework residue positions at which donor residues may be important or desirable for obtaining a CDR-grafted antibody product having satisfactory binding properties. The CDR-grafted products usually have binding affinities of at least $10^5$ $M^{-1}$, preferably at least about $10^8$ $M^{-1.}$ or especially in the range $10^8$–$10^{12}$ $M^{-1}$. In principle, the present invention is applicable to any combination of anti-hTNFα donor and human acceptor antibodies irrespective of the level of homology between their sequences. Examples of human frameworks which may be used are KOL, NEWM, REI, EU, TUR, TEI, LAY and POM (refs. 7 and 8) and the like; for instance KOL and NEWM for the heavy chain and REI for the light chain and EU, LAY and POM for both the heavy chain and the light chain.

Also the constant region domains of the products of the invention may be selected having regard to the proposed function of the antibody in particular the effector functions which may be required. For example, the constant region domains may be human IgA, IgE, IgG or IgM domains. In particular, IgG human constant region domains may be used, especially of the IgG1 and IgG3 isotypes, when the humanised antibody molecule is intended for therapeutic uses, and antibody effector functions are required. Alternatively, IgG2 and IgG4 isotypes may be used when the humanised antibody molecule is intended for therapeutic purposes and antibody effector functions are not required, e.g. for simple blocking of TNF activity.

However, the remainder of the antibody molecules need not comprise only protein sequences from immunoglobulins. For instance, a gene may be constructed in which a DNA sequence encoding part of a human immunoglobulin chain is fused to a DNA sequence encoding the amino acid sequence of a functional polypeptide such as an effector or reporter molecule.

In further aspects the invention also includes DNA sequences coding for the recombinant and humanised antibody, e.g. CDR-grafted, heavy and light chains, cloning and expression vectors containing the DNA sequences, host cells transformed with the DNA sequences and processes for producing the recombinant and humanised, e.g. CDR-grafted, chains and antibody molecules comprising expressing the DNA sequences in the transformed host cells.

The general methods by which the vectors may be constructed, transfection methods and culture methods are well known per se. Such methods are shown, for instance, in references 12 and 13.

The DNA sequences which encode the anti-hTNFα antibody molecule amino acid sequences may be obtained by methods well known in the art. For example the anti-TNF coding sequences may be obtained by genomic cloning, or cDNA cloning from suitable anti-hTNFα producing hybridoma cell lines. Positive clones may be screened using appropriate probes for the heavy and light chain genes in question. Also PCR cloning may be used. DNA sequence coding for part or all of the antibody heavy and light chains may be synthesised as desired from the determined DNA sequence or on the basis of the corresponding amino acid sequence.

DNA coding for acceptor, e.g. human acceptor, sequences may be obtained in any appropriate way. For example DNA sequences coding for preferred human acceptor frameworks such as KOL, REI, EU and NEWM, are widely available to workers in the art, or may be readily synthetised on the basis of their known amino acid sequences (see refs. 7 & 8).

The standard techniques of molecular biology may be used to prepare DNA sequences coding for the chimeric and CDR-grafted humanised antibody products. Desired DNA sequences may be synthesised completely or in part using oligonucleotide synthesis techniques. Site-directed mutagenesis and polymerase chain reaction (PCR) techniques may be used as appropriate. For example oligonucleotide directed synthesis as described by Jones et al (ref. 14) may be used. Also oligonucleotide directed mutagenesis of a pre-existing variable region as, for example, described by Verhoeyen et al (ref. 5) or Riechmann et al (ref. 6) may be used. Also enzymatic filling in of gapped oligonucleotides using $T_4$ DNA polymerase as, for example, described by Queen et al (ref. 9) may be used.

Any suitable host cell/vector system may be used for expression of the DNA sequences coding for the recombinant, chimeric and CDR-grafted humanised antibody heavy and light chains. Bacterial e.g. *E. coli*, and other microbial systems may be used, in particular for expression of antibody fragments such as Fab and F(ab')$_2$ fragments, and especially Fv fragments and single chain antibody fragments e.g. single chain Fvs. Eucaryotic e.g. mammalian host cell expression systems may be used for production of larger CDR-grafted antibody products, including complete antibody molecules, and/or if glycosylated products are required. Suitable mammalian host cells include CHO cells and myeloma or hybridoma cell lines.

Thus, in a further aspect the present invention provides a process for producing a recombinant or humanised anti-hTNFα antibody product comprising:

(a) producing in an expression vector an operon having a DNA sequence which encodes an anti-hTNFα antibody heavy chain;

and/or (b) producing in an expression vector an operon having a DNA sequence which encodes a complementary anti-hTNFα antibody light chain;

(c) transfecting a host cell with the or each vector; and (d) culturing the transfected cell line to produce the recombinant anti-hTNFα antibody product.

The recombinant or humanised anti-hTNFα product may comprise only heavy or light chain derived polypeptide, in which case only a heavy chain or light chain polypeptide coding sequence is used to transfect the host cells. For production of products comprising both heavy and light chains, the cell line may be transfected with two vectors, a first vector containing an operon encoding a light chain-derived polypeptide and a second vector containing an operon encoding a heavy chain-derived polypeptide. Preferably, the vectors are identical, except in so far as the coding sequences and selectable markers are concerned, so as to ensure as far as possible that each polypeptide chain is equally expressed. Alternatively, a single vector may be used, the vector including the sequences encoding both light chain- and heavy chain-derived polypeptides.

The DNA in the coding sequences for the light and heavy chains may comprise cDNA or genomic DNA or both.

The invention also includes therapeutic and diagnostic compositions comprising the recombinant and humanised antibody products of the invention and the uses of these products and the compositions in therapy and diagnosis.

Thus in a further aspect the invention provides a therapeutic or diagnostic composition comprising a recombinant or humanised antibody according to the invention in combination with a pharmaceutically acceptable excipient, diluent or carrier.

The invention also provides a process for the preparation of a therapeutic or diagnostic composition comprising admixing a recombinant or humanised antibody according to the invention together with a pharmaceutically acceptable excipient, diluent or carrier.

The recombinant or humanised antibody may be the sole active ingredient in the therapeutic or diagnostic composition or may be accompanied by one or more other active ingredients including other antibody ingredients, e.g. anti-T cell, anti-IFNγ or anti-LPS antibodies, or non-antibody ingredients such as xanthines. The therapeutic and diagnostic compositions may be in unit dosage form, in which case each unit dose comprises an effective amount of the recombinant or humanised antibody of the invention.

Furthermore, the invention also provides methods of therapy and diagnosis comprising administering an effective amount of a recombinant or humanised antibody according to the invention to a human or animal subject.

The antibodies and compositions may be utilised in any therapy where it is desired to reduce the level of TNF present in the human or animal body. The TNF may be in circulation in the body or present in an undesirably high level localised at a particular site in the body.

For example, elevated levels of TNF are implicated in immunoregulatory and inflammatory disorders and in septic, or endotoxic, and cardiovascular shock. The antibody or composition may be utilised in therapy of conditions which include sepsis, septic or endotoxic shock, cachexia, adult respiratory distress syndrome, AIDS, allergies, psoriasis, T.B., inflammatory bone disorders, blood coagulation disorders, burns, rejection episodes following organ or tissue transplant and autoimmune disease e.g. organ specific disease such as thyroiditis or non-specific organ diseases such as rheumatoid and osteo-arthritis.

Additionally, the antibody or composition may be used to ameliorate side effects associated with TNF generation during neoplastic therapy and also to eliminate or ameliorate shock related symptoms associated with the treatment or prevention of graft rejection by use of an antilymphocyte antibody, or may be used for treating multi-organ failure (MOF).

The recombinant and humanised antibodies and compositions of the invention are preferably for treatment of sepsis or septic/endotoxic shock.

The antibodies and compositions may be for administration in any appropriate form and amount according to the therapy in which they are employed. This may be for prophylactic use, for example where circumstances are such that an elevation in the level of TNF might be expected or alternatively, they may be for use in reducing the level of TNF after it has reached an undesirably high level or as the level is rising.

The therapeutic or diagnostic composition may take any suitable form for administration, and, preferably is in a form suitable for parenteral administration e.g. by injection or infusion, for example by bolus injection or continuous infusion. Where the product is for injection or infusion, it may take the form of a suspension, solution or emulsion in an oily or aqueous vehicle and it may contain formulatory agents such as suspending, preservative, stabilising and/or dispersing agents.

Alternatively, the antibody or composition may be in dry form, for reconstitution before use with an appropriate sterile liquid.

If the antibody or composition is suitable for oral administration, e.g. in the case of antibody fragments, the formulation may contain, in addition to the active ingredient, additives such as: starch—e.g. potato, maize or wheat starch or cellulose—or starch derivatives such as microcrystalline cellulose; silica; various sugars such as lactose; magnesium carbonate and/or calcium phosphate. It is desirable that, if the formulation is for oral administration it will be well tolerated by the patient's digestive system. To this end, it may be desirable to include in the formulation mucus formers and resins. It may also be desirable to improve tolerance by formulating the antibody or compositions in a capsule which is insoluble in the gastric juices. It may also be preferable to include the antibody or composition in a controlled release formulation.

In a still further aspect of the invention, there is provided a method of treatment of a human or animal subject suffering from or at risk of a disorder associated with an undesirably high level of TNF, the method comprising administering to the subject an effective amount of the antibody or composition of the invention. In particular, the human or animal subject may be suffering from, or at risk from, sepsis, or septic or endotoxic shock.

The dose at which the antibody is administered depends on the nature of the condition to be treated, the degree to which the TNF to be neutralised is, or is expected to be, raised above a desirable level, and on whether the antibody is being used prophylactically or to treat an existing condition. The dose will also be selected according to the age and conditions of the patient.

Thus, for example, where the product is for treatment or prophylaxis of septic shock suitable doses of antibody to TNF lie in the range 0.001–30 mg/kg/day, preferably 0.01–10 mg/kg/day and particularly preferably 0.1–2 mg/kg/day.

The antibody products may be used in diagnosis e.g. in in vivo diagnosis and imaging of disease states involving elevated TNF levels.

The invention is further described by way of illustration only in the following Examples which refers to the accompanying diagrams, FIGS. 1–6.

BRIEF DESCRIPTION OF THE FIGURES

FIG. 1 shows amino acid sequences for the variable domains of the heavy and light chains for the human acceptor antibody EU (1EU), the murine MAb CB0010 (htnf1) and humanised CDR grafted light (gEU) and heavy (2hEUg) chains. The amino acid sequences in FIG. 1 are represented as follows: Eu (light chain)—SEQ. ID NO: 1; htnf1 (light chain)—SEQ. ID NO: 2; gEu (light chain)—SEQ. ID NO: 3; Eu (heavy chain)—SEQ. ID NO: 4; htnf1 (heavy chain)—SEQ. ID NO: 5; 2hEug (heavy chain)—SEQ. ID NO: 6.

FIG. 2 shows amino acid sequences for the variable region domains of the human acceptor antibodies REI (1rei) for the light chain and KOL (KOL) for the heavy chain, of the heavy and light chains of the murine MAb 101.4 (101/4) and humanised grafted light and heavy chains (both designated g104). The amino acid sequences in FIG. 2 are represented as follows: rei (light chain)—SEQ. ID NO: 7; 101/4 (light chain)—SEQ. ID NO: 8; g1014—SEQ. ID NO: 9; KOL (heavy chain)—SEQ. ID NO: 10; 101/4 (heavy chain)—SEQ. ID NO: 11; g1014 (heavy chain)—SEQ. ID NO: 12.

FIG. 3 shows amino acid sequences for the variable region domains of the human acceptor antibodies REI (REI) for the light chain and KOL (KOL) for the heavy chain, of the heavy and light chains of the murine MAb CB0006 (CB6) and humanised grafted light and heavy chains (both designated gCB6). The amino acid sequences in FIG. 3 are represented as follows: REI (light chain)—SEQ. ID NO: 7; CB6 (light chain)—SEQ. ID NO: 13; gCB6 (light chain)—SEQ. ID NO: 14; KOL (heavy chain)—SEQ. ID NO: 10; CB6 (heavy chain)—SEQ. ID NO: 15; gCB6 (heavy chain)—SEQ. ID NO: 16.

FIG. 4 shows amino acid sequences for the variable region domains of the human acceptor antibodies REI (REI) for the light chain and KOL (KOL) for the heavy chain, of the heavy (HTNF3) and light (hTNF3) chains of the murine MAb HTNF3 and humanised grafted light (gHTNF3) and heavy (ghTNF3) chains. The amino acid sequences in FIG. 4 are represented as follows: REI (light chain)—SEQ. ID NO: 7; HTNF3 (light chain)—SEQ. ID NO: 17; gHTNF3 (light chain)—SEQ. ID NO: 18; KOL (heavy chain) —SEQ. ID NO: 10; hTNF3 (heavy chain)—SEQ. ID NO: 19; ghTNF3 (heavy chain)—SEQ. ID NO: 20.

FIG. 6 shows a graph comparing the ability of murine HTNF1 (CB0010) and CDR-grafted HTNF1 (CP571) to neutralise recombinant TNFα in the L929 bioassay.

DETAILED DESCRIPTION OF EMBODIMENTS OF THE INVENTION

EXAMPLE 1

CDR-Grafting of Murine Anti-TNFα Antibodies

Figure 5:
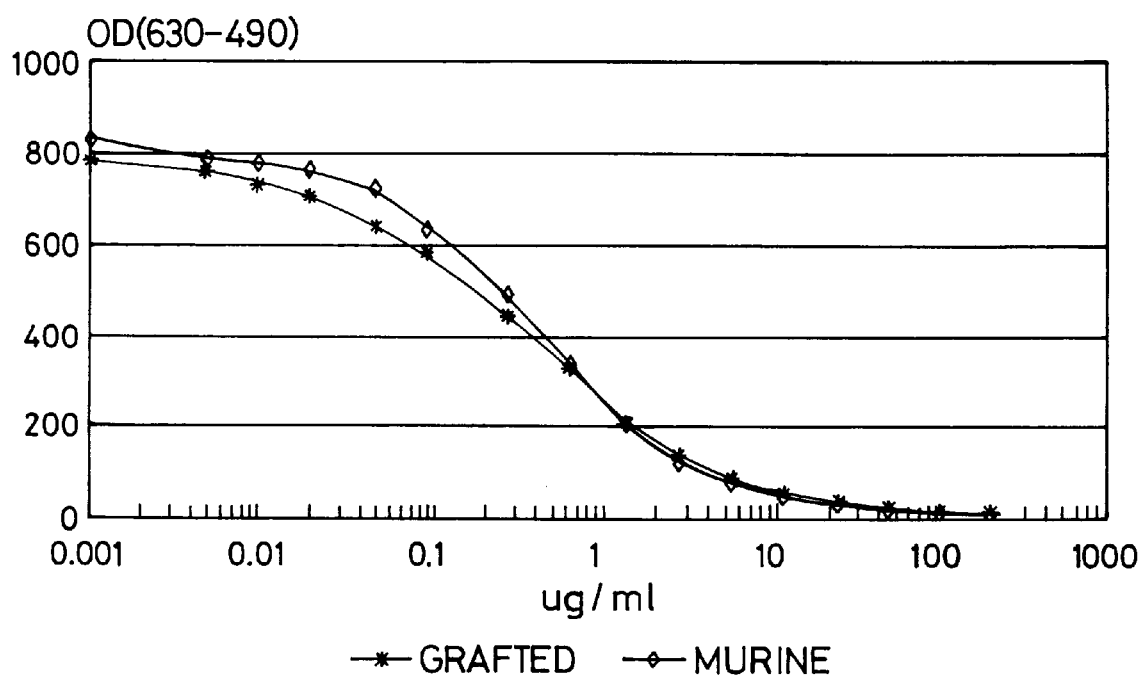
FIG. 5 shows a graph comparing the ability of murine CB0010 (hTNF1) and CDR-grafted CB0010 (GrhTNF1; CDP571) to compete with HRP-conjugated murine HTNF1 for binding to recombinant human TNFα.

A number of murine anti-human TNFα MAbs were CDR-grafted substantially as described in detail in WO91/09967 for the CDR-grafting of the murine anti-CD3 antibody OKT3. In this and subsequent Examples, the chimeric and CDR-grafted humanised antibodies were prepared using human IgG4 constant region domains, substantially as described for preparation of γ4 chimeric and CDR-grafted OKT3 antibodies in WO91/09967. It will be appreciated, however, that human constant region domains of other types and isotypes, e.g. IgG1, IgG2 and IgG3, could also have been used without significantly altering the procedures described.

These anti-hTNFα antibodies included the murine MAbs designated CB0006 (also known as 61E71), CB0010 (also known as hTNF1), hTNF3 and 101.4 A brief summary of the CDR-grafting of each of these antibodies is given below.

CB0006

A similar analysis as described in Example 1, Section 12.1. of WO91/09967 was carried out for CB0006 and for the heavy chain 10 framework residues were identified at positions 23, 24, 48, 49, 68, 69, 71, 73, 75 and 88 as residues to potentially retain as murine. The human frameworks chosen for CDR-grafting of this antibody, and the hTNF3 and 101.4 antibodies were RE1 for the light chain and KOL for the heavy chain. The amino acid sequences of the murine CB0006 (CB6) (heavy and Light) (SEQ. ID NO: 13 and SEQ. ID NO: 15) REI (REI) light (SEQ. ID NO: 7) and KOL (KOL) heavy chain (SEQ ID NO 10) variable domains are given in FIG. 3.

Three genes were built, the first of which coded for amino acid residues 23, 24, 48, 49, 71 and 73 [gH341(6)] as murine residues. The amino acid sequence of the variable domain coded by this first gene is shown as gCB6 in the heavy chain summary in FIG. 3. (SEQ. ID NO: 16) The second gene also had amino acid residues 75 and 88 as murine residues [gH341(8)] while the third gene additionally had amino acid residues 68, 69, 75 and 88 as murine residues [gH341(10)]. Each was co-expressed with gL221, the minimum grafted light chain (CDRs only) shown as gCB6 in the heavy chain summary in FIG. 3. (SEQ. ID NO: 14) The gL221/gH341(6) and gL221/gH341(8) antibodies both bound as well to TNF as murine 61E71. The gL221/gH341(10) antibody did not express and this combination was not taken further.

Subsequently the gL221/gH341(6) antibody was assessed in an L929 cell competition assay in which the antibody competes against the TNF receptor on L929 cells for binding to TNF in solution. In this assay the gL221/gH341(6) antibody was approximately 10% as active as murine CB0006.

CB0010 (also known as hTNF1)

CB0010 is a monoclonal antibody which recognises an epitope of human TNF-α. The EU human framework was used for CDR-grafting of both the heavy and light variable domains. The amino acid sequences of the heavy and light variable domains of EU (EU) (SEQ. ID NO: 4 and SEQ. ID NO: 1), CB0010 (htnf1) (SEQ. ID NO: 5 and SEQ. ID NO: 2) and grafted versions of CB0010 (gEU, light; 2hEUg, heavy) (SEQ. ID NO: 3 and SEQ. ID NO: 6) are shown in FIG. 1.

Heavy Chain

In the CDR-grafted heavy chain mouse CDRs were used at positions 26–35 (CDR1), 50–65 (CDR2) and 95–102 (CDR3). Mouse residues were also used in the frameworks at positions 48, 67, 69, 71, 73, 76, 89, 91, 94 and 108. Comparison of the TNF1 mouse and EU human heavy chain residues reveals that these are identical at positions 23, 24, 29 and 78.

Light Chain

In the CDR-grafted light chain mouse CDRs were used at positions 24–34 (CDR1), 50–56 (CDR2) and 89–97 (CDR3). In addition mouse residues were used in the frameworks at positions 3, 42, 48, 49, 83, 106 and 108. Comparison of the hTNF1 mouse and EU human light chain residues reveals that these are identical at positions 46, 58 and 71.

The grafted CB0010 heavy chain was co-expressed with the chimeric light chain and the binding ability of the product compared with that of the chimeric light chain/chimeric heavy chain product in a TNF binding assay. The grafted heavy chain product appeared to have binding ability for TNF slightly better than the fully chimeric product.

Similarly, a grafted heavy chain/grafted light chain product was co-expressed and compared with the fully chimeric product and found to have closely similar binding properties to the latter product. However when the grafted heavy chain/grafted light chain product was assayed in the L929 assay (see Example 4), it was found to have an activity only half that of the chimeric product. Thus further CDR-grafting experiments were carried out as described in Example 2.

hTNF3 hTNF3 recognises an epitope on human TNF-A. The sequence of hTNF3 shows only 21 differences compared to CB0006 in the light and heavy chain variable regions, 10 in the light chain (2 in the CDRs at positions 50, 96 and 8 in the framework at 1, 19, 40, 45, 46, 76, 103 and 106) and 11 in the heavy chain (3 in the CDR regions at positions 52, 60 and 95 and 8 in the framework at 1, 10, 38, 40, 67, 73, 87 and 105). The light and heavy chain variable domain amino acid sequences of hTNF3 (Htnf3, light; hTNF3, heavy), (SEQ. ID NO: 17 and SEQ. ID NO: 9) CDR-grafted hTNF3 (gHTNF3, light; ghTNF3, heavy) and REI (REI, light) (SEQ. ID NO: 7) and KOL (KOL, heavy) (SEQ. ID NO: 10) are shown in FIG. 4. The light and heavy chains of the CB0006 and hTNF3 chimeric antibodies can be exchanged without loss of activity in the direct binding assay. However CB0006 is an order of magnitude less able to compete with the TNF receptor on L929 cells for TNF-a compared to hTNF3. Based on the CB0006 CDR grafting data gL221 and gH341(+23, 24, 48, 49 71 and 73 as mouse) genes have been built for hTNF3 and tested and the resultant grafted antibody binds well to TNF-a, but competes very poorly in the L929 assay. The gL221 gene codes for the gHTNF3 and the gH341 etc. gene codes for the ghTNF3 variable domain sequences as shown in FIG. 4. (SEQ. ID NO: 18 and SEQ. ID NO: 20) It is likely that in this case other framework residues may need to be changed to improve the competitive binding ability of this antibody.

101.4

101.4 is a further murine MAb able to recognise human TNF-α. The heavy chain of this antibody shows good homology to KOL and so the CDR-grafting has been based on REI for the light chain and KOL for the heavy chain. The heavy and light variable domain amino acid sequences of 101.4 (101/4) (SEQ. ID NO: 8 and SEQ. ID NO: 11) and a CDR-grafted version of 101.4 (g1014) (SEQ. ID NO: 9 and SEQ. ID NO: 12) and the REI light chain (1rei) (SEQ. ID NO: 7) and KOL heavy chain (KOL) (SEQ. ID NO: 10) variable domains are given in FIG. 2. Several grafted heavy chain genes have been constructed with conservative choices for the CDR's (gH341) and which have one or a small number of non-CDR residues at positions 73, 78 or 77–79 inclusive, as the mouse amino acids. These have been co-expressed with the chimeric light chain or the Kabat CDR-grafted light chain. In all cases binding to TNF equivalent to the chimeric antibody is seen and when co-expressed with cL the resultant antibodies are able to compete well in the L929 assay. However, with gL221 the resultant antibodies are at least an order of magnitude less able to compete for TNF against the TNF receptor on L929 cells.

Mouse residues at other positions in the heavy chain, for example, at 23 and 24 together or at 76 have been demonstrated to provide no improvement to the competitive ability of the grafted antibody in the L929 assay.

EXAMPLE 2

Further CDR-Grafting of Murine anti-human TNFα Antibodies CB0010 and 101.4

Murine anti-human TNFα monoclonal antibodies CB0010 and 101.4 were further CDR-grafted substantially as described in WO91/09667.

CB0010

CB0010 is a monoclonal antibody which recognises an epitope on human TNF-α. The EU human framework was used for CDR-grafting of both the heavy and light variable domains.

The amino acid sequences of the heavy and light chain variable domains of the EU acceptor, (SEQ. ID NO: 1 and SEQ. ID NO: 4) CB0011 (htnf1) murine donor (SEQ. ID NO: 2 and SEQ. ID NO: 4) and CDR-grafted (gEU, light chain and 2hEUg, heavy chain) (SEQ. ID NO: 3 and SEQ. ID NO: 6) antibodies are given in FIG. 1.

Heavy Chain

In the CDR-grafted heavy chain (2hEUg) (SEQ. ID NO: 6), mouse CDRs were used at positions 31–35 (CDR1), 50–65 (CDR2) and 95–102 (CDR3).

Mouse residues were also used in the frameworks at positions 12, 27, 30, 38, 46, 48, 66, 67, 69, 71, 73, 76, 83, 89, 91, 94 and 108. Comparison of the CB0010 mouse and EU human heavy chain residues reveals that these are identical as positions 23, 24, 29 and 78.

Light Chain

In the CDR-grafted light chain (gEU) (SEQ. ID NO: 3) mouse CDRs were used at positions 24–34 (CDR1), 50–65 (CDR2) and 89–97 (CDR3). In addition mouse residues were used in the frameworks at positions 3, 42, 48, 49, 106 and 108. The human consensus residue (valine) was used at position 83. Comparison of the CB0010 mouse and EU human light chain residues reveals that these are identical at positions 46, 58 and 71.

The grafted CB0010 heavy chain was co-expressed with the chimeric light chain and the binding ability of the product compared with that of the chimeric light chain/chimeric heavy chain product in a TNF binding assay. The grafted heavy chain product appeared to have binding ability for TNF slightly better than the fully chimeric product.

Similarly, a grafted heavy chain/grafted light chain product was co-expressed and compared with the fully chimeric product and found to have closely similar binding properties to the latter product. The specific combination of grafted light chain (gEU) (SEQ. ID NO: 3) and grafted heavy chain (2hEUg) (SEQ. ID NO: 6), as shown in FIG. 1, provides the antibody known as CDP571. The murine CB0010 (CB0010), chimeric CB0010 (chimeric CB0010) and the grafted heavy chain/grafted light chain product(CDP571) were compared for binding to human TNFα in a standard assay. The results obtained are given in the table below in terms of the $K_D$ ($_p$M) measured for each antibody.

| Antibody | $K_D$ (pM) |
| --- | --- |
| CB0010 | 80 |
| Chimeric CB0010 | 81 |
| CDP571 | 87 |

The fully grafted antibody product (CDP571) is currently in pre-clinical development for treatment of sepsis syndrome and acute transplant rejection.

101.4

101.4 is a further murine MAb able to recognise human TNF-α. The heavy chain of this antibody shows good homology to KOL and so the CDR-grafting has been based on REI for the light chain and KOL for the heavy chain. An improved CDR-grafted product has been prepared. Variable domain amino acid sequences for REI (rei, light chain) (SEQ. ID NO: 7), KOL (KOL, heavy chain) (SEQ. ID NO: 10) murine 101.4 (101/4, heavy and light chain) (SEQ. ID NO: 8 and SEQ. ID NO: 11) and fully grafted antibody (g1014, heavy and light chain) (SEQ. ID NO: 9 and SEQ. ID NO: 12) are shown in FIG. 2.

Heavy Chain

In the CDR-grafted heavy chain (g1014) mouse CDRs were used at position 31–35 (CDR1), 50–65 (CDR2) and 95–102 (CDR3). Mouse residues were also used in the framework at positions 4, 11, 23, 24, 28, 73, 77, 78, 79, 91, 93, 94 and 108.

Light Chain

In the CDR-grafted light chain (g1014) mouse CDRs were used at positions 24–34 (CDR1), 50–56 (CDR2) and 89–97 (CDR3). In addition mouse residues were used in the framework at positions 1, 3, 4, 39, 73, 105 and 107. The human consensus residue (valine) was used at position 104.

The fully grafted heavy and light chain (g1014) were co-expressed and their binding to TNF compared with murine and chimeric 101.4 and also the fully grafted (gEU/2hEUg, CDP571) CB0010 antibody. The fully grafted 101.4 antibody was found to having binding properties for human TNFα similar to the murine, chimeric, and grafted CB0010 antibodies.

EXAMPLE 3

In vitro comparison of Murine and CDR-grafted Antibodies

A. Affinity Measurements for Murine CB0010 and CDP571

Materials and Methods

Materials

PBS/BSA: Dulbeccos PBS+1% (w/v) bovine serum albumin.

TNF: 50 nM rec. human TNF-alpha (Bissendorf Biochemicals), 0.85 μg/ml in PBS/BSA.

Stock $^{125}$I-TNF: 5 μCi, 185 kBq (Amersham International) dissolved in 500 μl water and stored at −70° C.

Working Solution $^{125}$I-TNF: ~62 pM for titration curve and 124 pM for Scatchard analysis, in PBS/BSA.

Antibodies: Purified murine CB0010 (mHTNF1) and CDP571 were quantified by A280 nm ($^{E}$1 mg/ml, 280 nm$^{=1.4}$), and diluted to a concentration of 1 μg/ml for titration, or 200 ng/ml for Scatchard analysis.

Immunobeads: Goat anti-murine IgG whole molecule-agarose or goat anti-human IgG whole molecule-agarose (Sigma) were used undiluted.

Method

Antibody titration: mHTNF1 and CDP571 were titrated in doubling dilutions (100 μl each) to give a total of 16 samples and $^{125}$I-TNF (100 μl, 62 pM) was added. The final top concentration of antibody was 500 ng/ml and $^{125}$I-TNF was 31 pM. Control tubes (8) contained $^{125}$I-TNF and PBS/BSA only. The samples were left to equilibrate overnight at room temperature, with shaking. After equilibration, 25 μl goat anti-mouse-agarose was added to the mHTNF1 samples, and 50 μl goat anti-human beads were added to the CDP571 samples except for the total $^{125}$I-TNF controls. Non-specific absorption of $^{125}$I-TNF to the agarose beads was corrected for by adding beads to 4 of the controls and comparing supernatant counts for these samples with those containing PBS/BSA instead of beads. After 1 hour equilibration at room temperature PBS/BSA (0.5 ml) was added and the samples were centrifuged at 1500 rpm for 10 mins at 20° C. The supernatant (0.5 ml) was removed and radioactivity was counted in a gamma counter.

Confirmation that $^{125}$I-TNF behaved similarly to the unlabelled material in this assay was made by performing the antibody titration in the presence of mixtures of $^{125}$I-TNF and unlabelled TNF (at 25% and 75% $^{125}$I-TNF) at the same total concentration.

Scatchard analysis: For both antibodies, unlabelled TNF (100 μl, 50 nM) was titrated in duplicate, in 13 doubling dilutions. One sample containing PBS/BSA in place of TNF was included for each antibody. $^{125}$I-TNF (50 μl, 124 pM) was added to each sample. A constant amount of antibody, determined from the titration curve (50 μl, 200 ng/ml) was then added.

This gave the following final concentrations: antibody, 50 ng/ml; TNF, 25 nM top concentration; $^{125}$I-TNF, 31 pM. The samples were left to equilibrate overnight and then treated exactly as for the antibody titration samples.

Calculations

Titration Curves $$\text{Bound }^{125}\text{I-TNF cpm} = \text{NSB cpm} - \text{supernatant cpm}$$

$$\frac{\text{Bound }^{125}\text{I-TNF cpm}}{\text{Total }^{125}\text{I-TNF}} = B/T$$

NSB = non-specific absorption blank, supernatant cpm

Total = total counts for $^{125}$I-TNF only

B/T was plotted against antibody concentration and the appropriate antibody concentration for use in Scatchard analyses was chosen at B/T=0.6

Scatchard Analysis

The mean of duplicate determination was used throughout

NSB=Total cpm−NSB supernatant cpm

Free cpm=sample cpm+NSB $$\frac{\text{sample cpm} + \text{NSB cpm}}{\text{Total cpm}} = B/F = \frac{1 - F/T}{F/T}$$

B/F was plotted against Bound TNF to give a slope of −1/Kd from which $K_d$ was calculated Results Dissociation Constants for Murine CB0010 and CDP571

| Antibody | $K_d$.M |
| --- | --- |
| Murine HTNF1 | 1.3 × 10$^{-10}$ |
| CDP571 | 1.4 × 10$^{-10}$ |

B. Competition of Murine CB0010 (Muhtnf1) and CDP571 (GrhTNF1) with HRP-Conjugated in Murine CB0010 for Binding to rhuTNF Method A 96 well microtitre plate (Nunc, Maxisorb) was coated with 100 μl/well TNF at 0.5 μg/ml.

Serial dilutions of murine or grafted antibody were prepared using PBS/1% BSA diluent, from 200 μg/ml to 0.1 μg/ml. 50 μl of antibody was added to each well followed by 50 μl HRP-murine CB0010 at 3 concentrations (0.625, 0.315 and 0.16 μg/ml). Plates were incubated for 2 hours at room temperature with agitation, washed 4 times with PBS and 100 μl of TMB substrate added. Optical Density was measured and OD plotted against antibody concentration.

Conclusions

Curves for both murine antibody (MuhTNF1) and grafted antibody (GrhTNF1) are superimposable, indicating both antibodies compete with similar affinity for binding to TNF (see FIG. 5).

EXAMPLE 4
Comparison of Murine CB0010 and CDR-grafted CDP571 Antibodies in Bioassay and Animal Model Experiments A. Neutralisation of TNF by CB0010 and CDP571 in the L929 Assay The ability of the parent murine antibody CB0010 (hTNF1) and the CDR-grafted antibody CDP571 to neutralise recombinant human TNF was determined using the L929 bioassay. The assay uses the L929 mouse fibroblastoid cell line which is killed by TNF. The assay is performed in the presence of 1 ug/ml actinomycin D which renders the cells more sensitive to TNF. Serial dilution of the two antibodies were mixed with a constant amount of recombinant human TNF (100 pg/ml) and added to a L929 monolayer in 96 well flat bottomed plates. After a 16 hour incubation the cells which had not been killed by TNF were revealed using the stain crystal violet. The apparent amount of TNF not neutralised (residual TNF) was determined by comparison with a recombinant TNF standard curve. Results from a representative experiment where residual TNF is plotted against antibody concentration are shown in FIG. 6. It can be seen that CB0010 and CDP571 have similar neutralisation activities.

B. Effect of CDP571 in Baboon Sepsis Model

In this study the effect of the prior treatment with CDP571 on the physiological consequences of severe sepsis (including death) was assessed. Baboons were chosen as a relevant species to study since CDP571 is known to neutralise baboon TNF.

Male adult baboons, *Papio ursinus*, weighting 20–25 kg were anaesthetised with ketamine hydrochloride and sodium pentabarbitone and instrumented for the measurement of blood pressure, cardiac index (by thermodilution), ECG and right atrial filling pressures. An infusion of either saline only or antibody was then given for 120 min at a rate of 2.5 ml/kg/h following which they were given a further 120 min infusion of live *E. coli* at the same infusion rate. The bacterial strain used was Hinshaw's strain B7 ([086a:61], ATCC 33985) administered whilst in the log growth phase at a dose of $2 \times 10^9$ CFU/kg giving a plasma concentration of $2-2.5 \times 10^5$ CFU/ml at the end of the infusion. Following a further 120 min, animals were returned to their home cages, given free access to food and water and monitored for cardiovascular changes twice a day for 3 days. All animals were given constant fluid replacement infusion of 5 ml/kg/h which was adjusted, where necessary, to maintain adequate right heart filling pressures. Baboons that had died during treatment or that had survived the 72 h experimental period, and then killed were post-mortemed. All major organs were assessed for gross macro-pathalogical damage according to semi-quantitative scale (+++ being the most severe).

Animals were randomly assigned to one of 4 treatment groups;

saline only

CDP571 0.1 mg/kg

CDP571 1.0 mg/kg

CB0010 0.1 mg/kg (parent murine antibody)

The survival and cumulative organ damage scores are shown in table 1. CDP571 at 1.0 mg/kg prevented death and significantly (P<0.005) reduced the incidence of organ damage in this model; furthermore, these effects were dose-related (P<0.005). In addition, the survival rate and organ damage score seen with CB0010 were similar to those seen with CDP571 at the same dose, indicating a maintained in vivo potency of CDP571 compared to its parent murine antibody.

TABLE 1

BABOON SEPSIS STUDY
SURVIVAL FOLLOWING ADMINISTRATION OF $2 \times 10^9$ CFU *E. Coli* GIVEN IV 2H AFTER SALINE OR CDP 571

| TREATMENT | No | DEAD | SURVIVED | PERCENT SURVIVAL | ORGAN PATHOL. |
|---|---|---|---|---|---|
| SALINE | 8 | 7 | 1 | 13 | +++ |
| CDP571 0.1 mg/kg | 6 | 2 | 4 | 67 | ++ |
| CDP571 1.0 mg/kg | 6 | 0 | 6 | 100 | +/– |
| CB0010 0.1 mg/kg | 4 | 1 | 3 | 75 | ++ |

References

1. Kohler & Milstein, Nature, 265, 295–497, 1975.
2. Chatenoud et al, (1986), J. Immunol. 137, 830–838.
3. Jeffers et al, (1986), Transplantation, 41, 572–578.
4. Begent et al, Br. J. Cancer 62: 487 (1990).
5. Verhoeyen et al, Science, 239, 1534–1536, 1988.
6. Riechmann et al, Nature, 332, 323–324, 1988.
7. Kabat, E. A., Wu, T. T., Reid-Miller, M., Perry, H. M., Gottesman, K. S., 1987, in Sequences of Proteins of Immunological Interest, US Department of Health and Human Services, NIH, USA.
8. Wu, T. T., and Kabat, E. A., 1970, J. Exp. Med. 132 211–250.
9. Queen et al, (1989), Proc. Natl. Acad. Sci. USA, 86, 10029–10033 and WO 90/07861.
10. Tempest et al, (1991), Biotechnology, 9, 266–271.
11. Beutler et al, (1985), Science, 234, 470–474.
12. Maniatis et al, Molecular Cloning, Cold Spring Harbor, N.Y., 1989.
13. Primrose and Old, Principles of Gene Manipulation, Blackwell, Oxford, 1980.
14. Jones et al, (1986), Nature, 321, 522.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 108 amino acids
        (B) TYPE: amino acid (D) TOPOLOGY: linear (ii) MOLECULE TYPE: protein (v) FRAGMENT TYPE: internal (xi) SEQUENCE DESCRIPTION: SEQ ID NO:1:

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Met
        35                  40                  45

Tyr Lys Ala Ser Ser Leu Glu Ser Gly Val Pro Ser Arg Phe Ile Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Asp Ser Lys
                85                  90                  95

Met Phe Gly Gln Gly Thr Lys Val Glu Val Lys Gly
            100                 105

(2) INFORMATION FOR SEQ ID NO:2:

(i) SEQUENCE CHARACTERISTICS:
        (A) LENGTH: 113 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

Asp Ile Met Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Ser Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asp Tyr Pro Trp Thr Phe Gly Gly Gly Ser Lys Leu Glu Ile
            100                 105                 110

Lys (2) INFORMATION FOR SEQ ID NO:3:

(i) SEQUENCE CHARACTERISTICS:
        (A) LENGTH: 114 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:3:

```
Asp Ile Met Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
                20                  25                  30

Asn Asn Gln Lys Asn Tyr Leu Ala Trp Tyr Gln Gln Lys Pro Gly Gln
            35                  40                  45

Ala Pro Lys Leu Leu Ile Ser Trp Ala Ser Thr Arg Glu Ser Gly Val
50                      55                  60

Pro Ser Arg Phe Ile Gly Ser Gly Ser Gly Thr Glu Phe Thr Leu Thr
65                      70                  75                  80

Ile Ser Ser Leu Gln Pro Asp Asp Val Ala Thr Tyr Tyr Cys Gln Gln
                85                  90                  95

Tyr Tyr Asp Tyr Pro Trp Thr Phe Gly Gln Gly Thr Lys Val Glu Ile
                100                 105                 110

Lys Arg
```

(2) INFORMATION FOR SEQ ID NO:4:

(i) SEQUENCE CHARACTERISTICS:
        (A) LENGTH: 117 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
                20                  25                  30

Ala Ile Ile Trp Val Arg Gln Ala Pro Gly Gln Gly Leu Glu Trp Met
            35                  40                  45

Gly Gly Ile Val Pro Met Phe Gly Pro Pro Asn Tyr Ala Gln Lys Phe
50                      55                  60

Gln Gly Arg Val Thr Ile Thr Ala Asp Glu Ser Thr Asn Thr Ala Tyr
65                      70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Trp Gly Gln Gly Thr Leu
                100                 105                 110

Val Thr Val Ser Ser
                115
```

(2) INFORMATION FOR SEQ ID NO:5:

(i) SEQUENCE CHARACTERISTICS:
        (A) LENGTH: 121 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:5:

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30
```

```
Asn Val Asp Trp Val Lys Gln Ser His Gly Lys Ser Leu Gln Trp Ile
            35                  40                  45

Gly Asn Ile Asn Pro Asn Asn Gly Gly Thr Ile Tyr Asn Gln Lys Phe
        50                  55                  60

Lys Gly Lys Gly Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Ser Ala Phe Tyr Asn Asn Tyr Glu Tyr Phe Asp Val Trp Gly
            100                 105                 110

Ala Gly Thr Thr Val Thr Val Ser Ser
            115                 120
```

(2) INFORMATION FOR SEQ ID NO:6:

(i) SEQUENCE CHARACTERISTICS:
        (A) LENGTH: 121 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:6:

```
Gln Val Gln Leu Val Gln Ser Gly Ala Glu Val Val Lys Pro Gly Ser
1               5                   10                  15

Ser Val Lys Val Ser Cys Lys Ala Ser Gly Tyr Thr Phe Thr Asp Tyr
            20                  25                  30

Asn Val Asp Trp Val Lys Gln Ala Pro Gly Gln Gly Leu Gln Trp Ile
            35                  40                  45

Gly Asn Ile Asn Pro Asn Asn Gly Gly Thr Ile Tyr Asn Gln Lys Phe
        50                  55                  60

Lys Gly Lys Gly Thr Leu Thr Val Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Ser Ala Phe Tyr Asn Asn Tyr Glu Tyr Phe Asp Val Trp Gly
            100                 105                 110

Gln Gly Thr Thr Val Thr Val Ser Ser
            115                 120
```

(2) INFORMATION FOR SEQ ID NO:7:

(i) SEQUENCE CHARACTERISTICS:
        (A) LENGTH: 107 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:7:

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
            35                  40                  45
```

```
Tyr Glu Ala Ser Asn Leu Gln Ala Gly Val Pro Ser Arg Phe Ser Gly
         50                  55                  60

Ser Ser Gly Thr Asp Tyr Thr Phe Thr Ile Ser Ser Leu Gln Pro Glu
 65                  70                  75                  80

Asp Ile Ala Thr Tyr Tyr Cys Gln Gln Tyr Gln Ser Leu Pro Tyr Thr
                 85                  90                  95

Phe Gly Gln Gly Thr Lys Leu Gln Ile Thr Arg
             100                 105
```

(2) INFORMATION FOR SEQ ID NO:8:

(i) SEQUENCE CHARACTERISTICS:
        (A) LENGTH: 108 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

```
Glu Ile Val Leu Thr Gln Ser Pro Pro Ile Met Ser Ala Ser Pro Gly
 1               5                  10                  15

Glu Lys Val Thr Met Thr Cys Ser Ala Ser Ser Val Ser Phe Met
                 20                  25                  30

Tyr Trp Tyr Gln Gln Lys Pro Gly Ser Ser Pro Arg Leu Leu Ile Tyr
             35                  40                  45

Asp Ala Ser Ile Leu Ala Ser Gly Val Pro Val Arg Phe Ser Gly Ser
         50                  55                  60

Gly Ser Gly Thr Ser Tyr Ser Leu Thr Ile Ser Arg Met Glu Ala Glu
 65                  70                  75                  80

Asp Val Ala Thr Tyr Tyr Cys Gln Gln Trp Ser Asp Tyr Ser Pro Arg
                 85                  90                  95

Thr Phe Gly Gly Gly Thr Lys Leu Glu Ile Lys Arg
             100                 105
```

(2) INFORMATION FOR SEQ ID NO:9:

(i) SEQUENCE CHARACTERISTICS:
        (A) LENGTH: 105 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:9:

```
Gln Ile Val Leu Thr Gln Ser Pro Ser Ser Leu Ser Ala Ser Val Gly
 1               5                  10                  15

Asp Arg Val Thr Ile Thr Cys Ser Ala Ser Ser Val Ser Phe Met
                 20                  25                  30

Tyr Trp Tyr Gln Gln Lys Pro Gly Lys Ala Pro Lys Leu Leu Ile Tyr
             35                  40                  45

Asp Ala Ser Ile Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Ile Ala Thr Tyr Tyr Cys Gln Gln Trp Ser Asp Tyr Ser Pro Arg
                 85                  90                  95
```

-continued

```
Thr Phe Gly Gln Gly Thr Lys Val Glu
            100                 105
```

(2) INFORMATION FOR SEQ ID NO:10:

(i) SEQUENCE CHARACTERISTICS:
        (A) LENGTH: 126 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:10:

```
Gln Val Gln Leu Val Glu Ser Gly Gly Val Val Gln Pro Gly Arg
1               5                   10                  15

Ser Leu Arg Leu Ser Cys Ser Ser Gly Phe Ile Phe Ser Ser Tyr
                20                  25                  30

Ala Met Tyr Trp Val Arg Gln Ala Pro Gly Lys Gly Leu Glu Trp Val
                35                  40                  45

Ala Ile Ile Trp Asp Asp Gly Ser Asp Gln His Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
                100                 105                 110

Pro Asp Tyr Trp Gly Gln Gly Thr Pro Val Thr Val Ser Ser
            115                 120                 125
```

(2) INFORMATION FOR SEQ ID NO:11:

(i) SEQUENCE CHARACTERISTICS:
        (A) LENGTH: 114 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:11:

```
Glu Val Lys Ile Glu Glu Ser Gly Gly Gly Trp Val Gln Pro Gly Gly
1               5                   10                  15

Ser Met Lys Leu Ser Cys Ile Ala Ser Gly Phe Thr Phe Ser Asn Tyr
                20                  25                  30

Trp Met Asn Trp Val Arg Gln Ser Pro Glu Lys Gly Leu Glu Trp Val
                35                  40                  45

Ala Glu Val Arg Leu Gln Ser Asp Asn Phe Thr Thr His Tyr Ala Glu
        50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Gly Ala Glu Asp Thr Gly Ile Tyr
                85                  90                  95

Tyr Cys Thr Pro Phe Ala Tyr Trp Gly Gln Gly Thr Leu Val Thr Val
                100                 105                 110

Ser Pro
```

(2) INFORMATION FOR SEQ ID NO:12:

(i) SEQUENCE CHARACTERISTICS:
    (A) LENGTH: 114 amino acids
    (B) TYPE: amino acid
    (D) TOPOLOGY: linear (ii) MOLECULE TYPE: protein (v) FRAGMENT TYPE: internal (xi) SEQUENCE DESCRIPTION: SEQ ID NO:12:

```
Gln Val Gln Ile Val Glu Ser Gly Gly Trp Val Gln Pro Gly Arg
1               5                   10                  15

Ser Leu Arg Leu Ser Cys Ile Ala Ser Gly Phe Thr Phe Ser Asn Tyr
                20                  25                  30

Trp Met Asn Trp Val Arg Gln Ala Pro Gly Lys Gly Leu Glu Trp Val
            35                  40                  45

Ala Glu Val Arg Leu Gln Ser Asp Asn Phe Thr Thr His Tyr Ala Glu
50                      55                  60

Ser Val Lys Gly Arg Phe Thr Ile Ser Arg Asp Asp Ser Lys Asn Gly
65                  70                  75                  80

Val Tyr Leu Gln Met Asp Ser Leu Arg Pro Glu Asp Thr Gly Val Tyr
                85                  90                  95

Tyr Cys Thr Pro Phe Ala Tyr Trp Gly Gln Gly Thr Leu Val Thr Val
            100                 105                 110

Ser Ser
```

(2) INFORMATION FOR SEQ ID NO:13:

(i) SEQUENCE CHARACTERISTICS:
        (A) LENGTH: 107 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:13:

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Ser Gly Gln Ser Pro Lys Val Leu Ile
            35                  40                  45

Tyr His Val Ser Asn Arg Tyr Thr Gly Val Pro Asp Arg Phe Thr Gly
50                  55                  60

Ser Gly Tyr Gly Thr Asp Phe Thr Phe Thr Ile Thr Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105
```

(2) INFORMATION FOR SEQ ID NO:14:

(i) SEQUENCE CHARACTERISTICS:
        (A) LENGTH: 108 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:14:

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
                20                  25                  30

Val Ala Trp Tyr Gln Gln Thr Pro Gly Lys Ala Pro Lys Leu Leu Ile
            35                  40                  45

Tyr His Val Ser Asn Arg Tyr Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Asp Tyr Ser Ser Pro Trp
                85                  90                  95

Thr Phe Gly Gln Gly Thr Lys Leu Gln Ile Thr Arg
            100                 105

(2) INFORMATION FOR SEQ ID NO:15:

(i) SEQUENCE CHARACTERISTICS:
        (A) LENGTH: 118 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:15:

Gln Ile Gln Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Thr Pro Gly Lys Gly Leu Lys Trp Met
            35                  40                  45

Gly Trp Ile Asn Thr Tyr Thr Gly Glu Pro Thr Tyr Asp Asp Asp Phe
    50                  55                  60

Lys Gly Arg Pro Ala Phe Ser Leu Glu Ala Ser Ala Ser Thr Ala Tyr
65                  70                  75                  80

Leu Gln Ile Asn Asn Leu Lys Asn Glu Asp Met Ala Thr Phe Phe Cys
                85                  90                  95

Ala Arg Gln Glu Gly Phe Tyr Ala Met Asp Tyr Trp Gly Gln Gly Thr
            100                 105                 110

Ser Leu Thr Val Ser Ser
        115

(2) INFORMATION FOR SEQ ID NO:16:

(i) SEQUENCE CHARACTERISTICS:
        (A) LENGTH: 117 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:16:

Gln Val Gln Leu Val Glu Ser Gly Gly Gly Val Val Gln Pro Gly Arg
1               5                   10                  15

-continued

```
Ser Leu Arg Leu Ser Cys Lys Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Gly Glu Pro Thr Tyr Asp Asp Asp Phe
    50                  55                  60

Lys Gly Arg Phe Thr Ile Ser Leu Asp Ala Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gln Glu Gly Phe Tyr Ala Met Asp Tyr Trp Gly Gln Gly Thr
                100                 105                 110

Pro Val Thr Val Ser
        115
```

(2) INFORMATION FOR SEQ ID NO:17:

(i) SEQUENCE CHARACTERISTICS:
  (A) LENGTH: 107 amino acids
  (B) TYPE: amino acid
  (D) TOPOLOGY: linear (ii) MOLECULE TYPE: protein (v) FRAGMENT TYPE: internal (xi) SEQUENCE DESCRIPTION: SEQ ID NO:17:

```
Asn Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asn Asp
            20                  25                  30

Val Ala Trp Tyr Gln Gln Lys Pro Gly Gln Ser Pro Arg Leu Leu Ile
        35                  40                  45

Tyr Tyr Val Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Val Gln Ala
65                  70                  75                  80

Glu Asp Leu Ala Tyr Tyr Phe Cys Gln Gln Asp Tyr Ser Ser Pro Tyr
                85                  90                  95

Thr Phe Gly Gly Gly Thr Arg Leu Glu Val Lys
                100                 105
```

(2) INFORMATION FOR SEQ ID NO:18:

(i) SEQUENCE CHARACTERISTICS:
  (A) LENGTH: 108 amino acids
  (B) TYPE: amino acid
  (D) TOPOLOGY: linear (ii) MOLECULE TYPE: protein (v) FRAGMENT TYPE: internal (xi) SEQUENCE DESCRIPTION: SEQ ID NO:18:

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Thr Pro Gly Lys Ala Pro Lys Leu Leu Ile
        35                  40                  45
```

```
Tyr Tyr Val Ser Asn Arg Tyr Thr Gly Val Pro Ser Arg Phe Ser Gly
     50                  55                  60

Ser Gly Ser Gly Thr Asp Tyr Thr Phe Thr Ile Ser Ser Leu Gln Pro
 65              70                  75                      80

Glu Asp Ile Ala Thr Tyr Tyr Cys Gln Gln Asp Tyr Ser Ser Pro Tyr
                 85                  90                  95

Thr Phe Gly Gln Gly Thr Lys Leu Gln Ile Thr Arg
            100                 105
```

(2) INFORMATION FOR SEQ ID NO:19:

(i) SEQUENCE CHARACTERISTICS:
        (A) LENGTH: 118 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:19:

```
Arg Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                 20                  25                  30

Gly Met Asn Trp Val Thr Gln Ala Pro Gly Lys Gly Leu Lys Trp Met
         35                  40                  45

Gly Trp Ile Asn Thr Tyr Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65              70                  75                      80

Leu Gln Ile Asn Asn Leu Lys Asn Glu Asp Thr Ala Thr Tyr Phe Cys
                 85                  90                  95

Ala Arg Lys Glu Gly Phe Tyr Ala Met Asp Tyr Trp Gly Gln Gly Thr
            100                 105                 110

Ser Val Thr Val Ser Ser
            115
```

(2) INFORMATION FOR SEQ ID NO:20:

(i) SEQUENCE CHARACTERISTICS:
        (A) LENGTH: 117 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:20:

```
Gln Val Gln Leu Val Glu Ser Gly Gly Val Val Gln Pro Gly Arg
 1               5                  10                  15

Ser Leu Arg Leu Ser Cys Lys Ala Ser Gly Tyr Thr Phe Thr Asn Tyr
                 20                  25                  30

Gly Met Asn Trp Val Arg Gln Ala Pro Gly Lys Gly Leu Glu Trp Met
         35                  40                  45

Gly Trp Ile Asn Thr Tyr Thr Gly Glu Pro Thr Tyr Ala Asp Asp Phe
     50                  55                  60

Lys Gly Arg Phe Thr Ile Ser Leu Asp Thr Ser Lys Asn Thr Leu Phe
 65              70                  75                      80
```

-continued

```
Leu Gln Met Asp Ser Leu Arg Pro Glu Asp Thr Gly Val Tyr Phe Cys
                85                  90                  95

Ala Arg Lys Glu Gly Phe Tyr Ala Met Asp Tyr Trp Gly Gln Gly Thr
            100                 105                 110

Pro Val Thr Val Ser
            115
```

We claim:

1. An antibody moldcule which has specificity for human TNFα comprising a heavy chain and a light chain, said heavy chain having a variable domain comprising an amino acid sequence selected from the group consisting of SEQ ID: NO. 6, SEQ ID: NO. 12, SEQ ID: NO. 16, and SEQ ID: NO. 20.

2. An antibody molecule which has specificity for human TNFα comprising a light chain and a heavy chain, said light chain having a variable chain comprising an amino acid sequence selected from the group of SEQ ID: NO. 3, SEQ ID: NO. 9, SEQ ID: NO. 14, and SEQ ID: NO. 18.

3. An antibody molecule which has specificity for human TNFα comprising a heavy chain having a variable domain comprising the amino acid sequence of SEQ ID: NO. 6 and a light chain having a variable domain comprising the amino acid sequence of SEQ ID: NO. 3.

* * * * *